United States Patent [19]

Popov et al.

[11] 4,348,481
[45] Sep. 7, 1982

[54] METHOD OF OBTAINING GLUCOSE ISOMERASE

[75] Inventors: Mitko S. Popov; Galina M. Djedjeva; Ivan O. Todorov; Nelly S. Stoeva, all of Sofia, Bulgaria

[73] Assignee: Institute Po Microbiologia, Sofia, Bulgaria

[21] Appl. No.: 212,094

[22] Filed: Dec. 2, 1980

[30] Foreign Application Priority Data

Nov. 29, 1979 [BG] Bulgaria .................. 45750

[51] Int. Cl.³ .............................. C12N 9/92
[52] U.S. Cl. ...................... 435/234; 435/886
[58] Field of Search ........................ 435/234

[56] References Cited

U.S. PATENT DOCUMENTS

| | | | |
|---|---|---|---|
| 3,616,221 | 10/1971 | Takasaki et al. | 435/234 |
| 3,623,953 | 11/1971 | Cotter et al. | 435/234 |
| 3,625,828 | 12/1971 | Brownwell | 435/234 |
| 3,708,397 | 1/1973 | Sipos | 435/234 |
| 3,826,714 | 7/1974 | Suekane et al. | 435/234 X |
| 3,956,066 | 5/1976 | Coker et al. | 435/234 X |
| 3,979,261 | 9/1976 | Outtrup | 435/234 |
| 4,061,539 | 12/1977 | Lee | 435/234 X |
| 4,255,521 | 3/1981 | Hirohara et al. | 435/234 |
| 4,283,496 | 8/1981 | Lee | 435/253 |
| 4,291,123 | 9/1981 | Degnen | 435/94 |

*Primary Examiner*—Lionel M. Shapiro
*Attorney, Agent, or Firm*—Karl F. Ross

[57] ABSTRACT

A method of obtaining glucose isomerase which comprises cultivating the enzyme-producing strain Streptomyces sp. N.765, registration No. 143 (Bulgarian State Institute for Drug Control, Sofia, Bulgaria,) for 36 to 72 hours at a temperature of 24° to 36° C. at an initial pH of 6.5 to 9.0 in a culture medium containing 1.0 to 2.0% xylose 1.5 to 4.0% of dry weight of maize extract and 0.23 to 1.0% weight sodium acetate.

3 Claims, No Drawings

METHOD OF OBTAINING GLUCOSE ISOMERASE

The invention relates to a method of obtaining of glucose isomerase from a streptomyces strain.

It is known that by means of the enzyme glucose isomerase D-glucose is transformed into D-fructose, which finds increasingly wider application in the food processing industry and in dietic feeding in a number of developed countries. Glucose isomerase, in combination with a complex of amylolytic enzymes ($\alpha$ amylase and glucoamylase), permits glucose-fructose syrups and fructose to be obtained directly from starch, using enzymes. Some methods for obtaining of glucose isomerase have been known since 1957 when the possibility of direct conversion of D-glucose into D-fructose through the cells of the bacterial strain *Pseudomonos hydrophila* N.491 and N.492 was demonstrated for the first time. For obtaining of glucose isomerase microorganisms of thegenus Streptomyces, are most widely used. It has been found that the presence of different mineral salts in the cultivation medium is a necessary condition for the biosynthesis of the enzyme glucose isomerase. In the culture media, described in the literature and in patents, magnesium salts are present in the form of $MgSO_4.7H_2O$ and cobalt in the form of $CoCl_2.6H_2O$. The concentrations in which these salts are introduced into the cultivation medium depends on the type microorganism and vary most frequently from 0.02 to 0.5% for $MgSO_4.7H_2O$ and from 0.005 to 0.024% for $CoCl_2.6H_2O$. With some streptomyces species, cobalt is absolutely necessary for the formation of glucose isomerase, though the activation is carried out due to the magnesium ions.

It is necessary that some strains and mutant-producers of glucose isomerase should be discovered to produce a sufficient quantity of enzyme in the absence of cobalt ions in the cultivation medium. The mutants of CPC International Inc are known, as well as some Artrobacters, studied by R. J. Reynolds Tobacco, which don't require cobalt for the biosynthesis of glucose isomerase.

The addition of cobalt and magnesium ions to the glucose solutions during the isomerization also influences strongly enzyme activity. It was proved, that these metals are cofactors of the enzyme and that glucose isomerase can be referred to as metal enzymes. It has been found that one molecule of glucose isomerase belonging to Str.sp.YT N.5 contains 4.1 cobalt atoms and 33 magnesium atoms. It was supposed that the combination of $Mg^{++}$ and $Co^{++}$ with glucose isomerase was necessary for its transformation into an active form. It is also considered that during this process a change in the conformation of the enzyme takes place. Some authers assume that the introduction of cobalt ions, especially together with magnesium ions considerably increases the thermostability of glucose isomerase.

The presence of higher quantities of $Co^{++}$ in fructose syrups is undesirable, although traces of $Co^{++}$ are necessary for the nutrition of man. The content of $Co^{++}$ ions in the fructose syrup is about 1 mM, but this concentration causes certain toxic effects on rats. For the separation of the cobalt ions from the glucose isomerase syrups when isomerization process is over, they must necessarily be cultivated with ion-exchange resins to maximum separation. Industrial automatic ion-exchange systems are required for this additional process.

Mi-Car International uses some completely automated ion-exchange systems consisting of two cation-anion parts (strongly acidic cation-exchange resin Duolite C25-D and weakly basic anion resin Duolite S-56). This ion-exchange system needs periodical regeneration with acids or bases and large additional quantities of clean water.

The content of cobalt ions in the glucose-fructose syrups, which have been processed in the ion-exchange system, is controlled with the help of an automatic absorption spectrophotometer, by means of tests, constantly withdrawn from the stream. Thus the operation of the cation-exchange system is regulated. In this processing $Co^{++}$ ions must be removed effectively so that they shouldn't exceed 5ppb with 25% S.

This process complicates the production and influences the effectivity and the cost of the product.

The object of this invention is to provide a method for obtaining of glucose isomerase from a strain producer of industrial capability, wherein cobalt ions are not necessary for the biosynthesis of the enzyme and for the isomerization of D-glucose into D-fructose.

Strain Streptomyces sp. N.765, a producer of glucose isomerase, has been isolated from Bulgarian soil. 874 streptomyces strains were screened for its discovery. The screening was carried out on the modified synthetic culture medium N.1 after Krassilnikov the selection being realized on two substrate levels with the use of xylose and xylane. Under these conditions 18 streptomyces strains were discovered which can develop and produce the enzyme glucose isomerase. Among them is the strain Streptomyces sp. N.765 which is capable of producing the enzyme glucose isomerase in the absence of $Co^{++}$ in the cultivation medium. The strain is on deposit in the State Institute for Drugs Control—bul.-Vladimir Zaimov N.26 on Sept. 29, 1979 under N. 143, is available upon request and will remain on deposit with availability of access to the public, and has the following morphological and biochemical characteristics:

On culture medium 1 with a mineral source of nitrogen (after G. F. Gause and collaborators) the colonies are usually oval in shape with unshaped edges, convex in the center swollen with a crater like cavity with strongly expressed radial folds. The growth is good. The sporangia in young cultures are elongated, monopodially situated with 3–5 coils and in older cultures they are condensed in sorghum.

The spores are elongated with rounded ends: when they are magnified more than 16,000 times some hair-like formations can be observed on their surface. On a weaker magnification in the spores look smooth. Their size varies between 0.9–1.2 microns in length and 0.4–0.6 microns in width.

The color of the air mycelium and substrate mycelium is determined according to the color scale of A. C. Bondartsev and the scale of Tresner and Backus. With the different culture media the color of the air mycelium changes from white ($d^1$) light-grey to violet ($a^5$–$d^3$) depending on the carbon and nitrogen sources. On culture medium 1 with a mineral source of nitrogen (after G. F. Gause and collaborators) the color is light-grey to mousy-grey ($a^5$–$a^3$) and on a culture medium with an organic source of nitrogen (after G. F. Gause and col.) the color is dark-grey to grey-violet ($a^2$–$a^3$).

On culture media with different carbon and nitrogen sources the air mycelium is greyish green.

On culture medium 1 with a mineral source of nitrogen (after G. F. Gause and collaborators) the substrate mycelium is dove-colored to ultramarine ($1^6$–$v^1$).

On culture medium 2 with an organic source of nitrogen (after G. F. Gause and collaborators) it is ultramarine ($v^1$), and after prolonged cultivation becomes black ($a^1$).

On culture media with different carbon and nitrogen sources the substrate mycelium is from dark-red to black.

On the culture medium meat-pepton agar, there was low growth. Air mycelium—pink and brick-red along the edge. Substrate mycelium—brick-red.

On the culture medium potato glucose agar, growth was very good. Air mycelium—grey-blue. Substrate mycelium—blue to dark-blue. On the culture medium Tchapek with sucrose. Low growtn. Air mycelium—pink. Substrate mycelium—light-brick.

On Tchapek with glucose, there was medium growth. Air mycelium—light-blue. Substrate mycelium colorless with a shade of the air mycelium.

On culture medium with sucrose; Good growth. Air mycelium—sky-blue. Substrate mycelium—dark-blue to black.

On cultural medium amylium agar; Good growth. Air mycelium—grey. Substrate mycelium—blue.

On amylum-ammonia culture, after Mishustin; Very good growth. Air mycelium—grey. Substrate mycelium wine-red to dark wine-red.

On synthetic medium after N. A. Krassilnikov; Medium growth. Air mycelium light-ashy-colored. Substrate mycelium—pink-violet.

On CPI after N. A. Krassilnikov; Good growth. Air mycelium—grey-blue. Substrate mycelium—red-brown.

On CPII after N. A. Krassilnikov; Growth low to medium. Air mycelium—blue. Substrate mycelium—dark cream-colored.

On CPII after N. A. Krassilnikov; Growth good. Air mycelium grey to ultramarine. Substrate mycelium wine-red. On CPIV after N. A. Krassilnikov; Low growth. Air mycelium light-grey. Substrate mycelium colorless, with a shade of the air mycelium color.

On CPV after N. A. Krassilnikov; Good growth. Air mycelium—grey. Substrate mycelium—dark-violet.

On synthetic culture medium after Vaxman; Medium growth. Air mycelium grey to mousy-grey. Substrate mycelium dark cream-colored to red-brown.

On meat-amylum agar. Low growth. Air mycelium—white. Substrate cream-colored.

On peptone agar. Good growth; Air mycelium—grey. Substrate coloress with a grey shade of the air mycelium color.

On glucose-asparagine agar: Very good growth. Air mycelium—grey to ultramarine. Substrate mycelium blue-violet to dark-blue.

On glycerine-asparagine agar: Good growth. Air mycelium—ultramarine. Substrate mycelium dark-violet to black.

On tyrosine culture medium: Good growth. Air mycelium—blue-grey, ultramarine. Substrate mycelium—red-brown.

On tyrosine-caseine-nitrate agar: Low growth. Air mycelium—white. Substrate mycelium—cream-colored.

On glucose-tyrosine agar: Medium growth. Air mycelium—cream-grey. Substrate mycelium—violet.

On saccharese-nitrate agar: Good growth. Air mycelium—grey to ultramarine. Substrate mycelium—blue to dark blue.

On glycerol-calcium-malate agar: Good growth. Air mycelium—blue to ultramarine.

On peptone-beef agar: Medium good growth. Air mycelium—grey. Substrate mycelium—colorless with a grey shade of the air mycelium.

On oats agar: Medium growth. Air mycelium—grey. Substrate mycelium—wine-red.

On tomato agar: Good growth. Air mycelium—grey. Substrate mycelium—dark-beige, terracotta color.

On lead-acetate agar: Low growth. Air mycelium brown. Substrate mycelium colorless with a shade of the air mycelium color.

On iron-peptone agar. Good growth. Air mycelium—colorless gray. Substrate mycelium—colorless with a grey shade of the air mycelium.

On yeast-malt agar. Medium growth. Air mycelium—grey, mousy grey. Substrate mycelium dark cream-colored.

Strain tolerance towards NaCl. It shows low tolerance towards the concentration of sodium chloride in the medium. The maximum concentration is 4%. Under this concentration the strain growth is low. The air mycelium is light-blue. The substrate mycelium is dark-blue. A concentration higher than 2% NaCl has a negative influence on the degree of sporulation. It coagulates fatless milk. It doesn't condense gelatine. It grows well on sucrose medium, but doesn't invert sucrose. It grows very well on an amylum agar and hydrolyzes starch well. It doesn't decompose cellulose and reduces nitrates to nitrites. It liberates hydrogen sulphide. It grows on potatos. Hemolysis—negative. Tyrosinase—positive, it forms melanoids.

It has been found out that on basic culture medium of Pridham and Gottlieb the growth is good in the presence of the following carbon sources: glucose, fructose, lactose, levulose, xylose, manose, cellulose, galactose, mannite, inosite, arabinose, dextrine, ribose and glycerol.

The strain absorbs salicin on a small scale.

It doesn't grow on culture medium with sorbite, sucrose and raffinose. Some differences in the pigmentation of the air mycelium and the substrate mycelium are observed, depending on the source of carbon.

The growth of the strain is good on modified basic culture medium of Prudham and Gottlieb with the following sources of nitrogen: $NH_4Cl$, $(NH_4)_2SO_4$; $(NH_4)_2HPO_4$; $NH_4H_2PO_4$ and carbamide.

The growth is moderate on a culture medium with $NH_4NO_3$ and $Na_2HPO_4$. The strain does not grow at all on a culture medium with $NaNO_3$ and $NaNO_2$.

A very good growth of the strain is observed on culture media with the following aminoacids:

glutamic acid, asparaginic acid, alanine, valine, asparagine. The growth is moderate on a culture medium with leucine, cystine, proline, xydroxyproline, phenylalanine and tyrosine. Depending on the source of nitrogen, some differences in the pigmentation of the air mycelium and the substrate mycelium are observed.

According to some characteristics streptomyces strain N.765 resembles Streptomyces coelicolor, belonging to the series gray after Bergey's—1974 (Actinomyces coelicolor of the Coelicolor group after N. A. Krassilnikov—1970). The latter is distinguished by some morphological-cultural and physiological-biochemical properties, described in the species' characterization by Bergey's (1974) and N. A. Krassilnikov (1970). Streotomyces coelicolor for example, has from 1 to 3 coils of the spirals, it condenses gelatine slowly and peptonizes fatless milk. Its tyrosinase is negative. Therefore streptomyces strain N.765 is not identical with the similar *Streptomyces coelicolor* (*Actinomyces coelicolor*) and that is why it is referred to as Streptomyces sp.N.765 belonging to the Gray series after Bergey's (1974) and the Coelicolor group after N. A. Krassilnikov (1970). The strain-producer is cultivated in Erlenmeyer flasks of 500 ml containing 50 ml fermentation culture medium from 36 to 96 hours under a temperature of 24° to 36° C., initial pH of cultivation from 6.5 to 9.0, on a shaker at 180–320 revolutions per minute.

Isomerization of glucose to fructose by means of glucose isomerase of the strain Streptomyces sp. N.765 can be carried out through a direct treatment with fresh mycelium(separated through centrifugation at 12,000 revolutions per minute and washed three times with 0.05 M phosphate buffer with pH 7.0) or with dried mycelium(air-dried or acetone-dried cells) with enzyme solution (obtained after ultrasonic disintegration or autolysis of cell material and separation of supernatant through centrifugation at 15,000 rev./min. with cultural centrifugation, containing extracellular isomerase or cells made immobile on a hard carrier.

The fructose, formed in the reacting mixture determined according to the cystein-carbasole method and the activity of the strain is expressed in mg. of fructose per ml. cultural liquid or in International glucose isomerase units(GIU). One GIU is equal to the quantity of enzyme which under 70° C. and pH 7.0 1 M glucose solution in 0.05 M phosphate buffer, and $2.10^{-2}$M MgSO$_4$·7H$_2$O transforms in one minute 1 Mmol glucose into 1 μmol. fructose.

The preferred concentrations of MgSO$_4$·7H$_2$O and the substrate for the cultivation are respectively $1 \times 10^{-4}$ to $1 \times 10^{-2}$M and from 0.1 to 3 M respectively.

The advantages of the method according to the invention, are the following:

The strain Streotomyces sp. N.765 produces the enzyme glucose-isomerase in the absence of cobalt ions in the fermentation medium. The obtained enzyme transforms D-glucose into D-fructose in the absence of cobalt ions in the isomerization mixture, which considerably facilitates the technological process and it is not necessary to use ion-exchange systems for the separation of cobalt from the fructose-containing syrups. As compared with the strains, microorganisms and mutant-producers of glucose isomerase, known in patent literature, which do not require cobalt ions in the cultivation medium and in isomerization mixtures (2a,b,c; 9a,b), Streptomyces sp. N.765 excels them with its glucose isomerase activity, favourable pH optimum (7,0), higher temperature optimum (80°) of the enzyme and its considerable thermostability between 40° and 70° C.

1. Xylose culture medium:

| Xylose | 20 g. |
| agar | 20 g. |
| KNO$_3$ | 1.0 g. |
| K$_2$HPO$_4$ | 0.5 g. |
| MgSO$_4$·7H$_2$O | 0.5 g. |
| NaCl | 0.5 g. |
| CaCO$_3$ | 1.0 g. |
| FeSO$_4$ | 0.001 g. |
| water up to 1l. | |

2. Potato-glucose agar:
potato extract from 300 g. boiled potatoes

-continued

| glucose | 10 g. |
| agar | 20 g. |
| water up to 1l. | |

It is recommended that for the maintenance of the strain both culture media should be alternated.

To a well germinated material from 10–15 days culture on culture medium 1 or 2 (1 is recommended) 6 ml inoculation culture medium is added, having the following composition.

| xylose | 1,% |
| beef extract | 2% |
| MgSO$_4$·7H$_2$O | 0.1% |
| K$_2$HPO$_4$ | 0.3% |

A wach-out of the cell mass is carried out and the test-tube is put on a shaker for 24 hours under 30° C. and at 240 revolutions per minute. From thus adapted culture inoculation medium with the following composition is sown:

| Xylose | 1% | |
| maize extract | 2% | (in dry weight) |
| Na-acetate | 0.5% | |

The cultivation is carried out in Erlenmeyer flasks of 500 ml fermentation culture medium. It is carried out for 60 hours under 30° C. on a shaker at 240 revolutions per minute. The initial pH of cultivation is 8.5.

After 60 hours of cultivation of Streptomyces sp.N.765 it is obtained 160–240 g. humid biomass per 1l of cultural liquid. Example 2. Izomerization of glucose to fructose by means of glucose isomerase of the strain Streptomyces sp. N.765 is carried out under a temperature of 70° C., pH 7.0 in the presence of MgSO$_4$·7H$_2$O in concentration $2.10^{-2}$M and substrate concentration 1 M.

The activity of the strain Streptomyces sp. N.765 is 75–130 mg fructose per 1 ml cultural liquid or 7,000–12,000 GIU per 1l cultural liquid.

What we claim is:

1. A method for obtaining of glucose isomerase, wherein the enzyme-producing strain Streptomyces sp.N.765 registration N.143—State Institute for Drug Control, Sofia, Bulgaria, is cultivated for 36 to 72 hours in a culture medium with xylose as an inductor, the temperature being kept from 24° to 36° C., the initial pH of cultivation is from 6.5 to 9.0; the temperature of izomerization is from 50° to 90° C., pH is from 6.0 to 9.0 in the presence of MgSO$_4$·7H$_2$O in a concentration from $1.10^{-4}$ to $1.10^{-2}$M and substrate concentration from 0.1 to 3 M.

2. A method of obtaining glucose isomerase which comprises cultivating the enzyme-producing strain Streptomyces sp. N.765, registration No. 143 (Bulgarian State Institute for Drug Control, Sofia, Bulgaria,) for 36 to 72 hours at a temperature of 24° to 36° C. at an initial pH of 6.5 to 9.0 in a culture medium containing 1.0 to 2.0% xylose, 1.5 to 4.0% of dry weight of maize extract and 0.23 to 1.0% weight sodium acetate.

3. Method, according to claim 1, wherein the culture medium which is used has the following composition:

| xylose | 1.0–2.0% | |
| maize extract | 1.5–4.0% | (in dry weight) |
| Na-acetate | 0.25–1.0% | |

* * * * *